(12) United States Patent
Fleenor et al.

(10) Patent No.: US 7,803,824 B2
(45) Date of Patent: Sep. 28, 2010

(54) USE OF INHIBITORS OF JUN N-TERMINAL KINASES TO TREAT GLAUCOMA

(75) Inventors: Debra L. Fleenor, Crowley, TX (US); Iok-Hou Pang, Grand Prairie, TX (US)

(73) Assignee: Alcon, Inc., Hunenberg (CH)

( * ) Notice: Subject to any disclaimer, the term of this patent is extended or adjusted under 35 U.S.C. 154(b) by 756 days.

(21) Appl. No.: 11/394,893

(22) Filed: Mar. 31, 2006

(65) Prior Publication Data
US 2006/0172991 A1    Aug. 3, 2006

Related U.S. Application Data

(63) Continuation-in-part of application No. 11/259,566, filed on Oct. 26, 2005.

(60) Provisional application No. 60/623,755, filed on Oct. 29, 2004.

(51) Int. Cl.
*A61K 31/425* (2006.01)

(52) U.S. Cl. ..................................................... 514/367

(58) Field of Classification Search .................. 514/367
See application file for complete search history.

(56) References Cited

U.S. PATENT DOCUMENTS

| 6,451,787 B1 * | 9/2002 | Nakata et al. .......... 514/211.08 |
| 2004/0058875 A1 | 3/2004 | Gamache |
| 2004/0072888 A1 | 4/2004 | Bennett et al. |
| 2004/0092568 A1 | 5/2004 | Zeldis |
| 2004/0176434 A1 | 9/2004 | Bennett et al. |
| 2006/0094753 A1 | 5/2006 | Pang et al. |

FOREIGN PATENT DOCUMENTS

| EP | 1121932 | 8/2001 |
| EP | 1 193 256 A1 | 4/2002 |
| EP | 1 193 256 A8 | 4/2002 |
| EP | 1 426 050 A1 | 6/2004 |
| WO | WO 00/35906 A2 | 6/2000 |
| WO | WO 00/35906 A3 | 6/2000 |
| WO | WO 00/64872 A1 | 11/2000 |
| WO | WO 01/12609 A1 | 2/2001 |
| WO | WO 01/12621 A1 | 2/2001 |
| WO | WO 01/23378 A1 | 4/2001 |
| WO | WO 01/23379 A1 | 4/2001 |
| WO | WO 01/47920 A1 | 7/2001 |
| WO | WO 01/91749 A1 | 12/2001 |
| WO | WO 02/46170 A2 | 6/2002 |
| WO | WO 02/062792 A1 | 8/2002 |
| WO | WO 01/23382 A1 | 10/2002 |
| WO | WO 02/081475 A1 | 10/2002 |
| WO | WO 02/083648 A1 | 10/2002 |
| WO | WO 03/024967 A2 | 3/2003 |
| WO | WO 03/024967 A3 | 3/2003 |
| WO | WO 03/035909 A2 | 5/2003 |
| WO | WO 03/035909 A3 | 5/2003 |
| WO | WO 03/035921 A1 | 5/2003 |
| WO | WO 03/106455 A1 | 12/2003 |
| WO | 2006050045 | 5/2006 |
| WO | WO 2006/050045 A2 | 5/2006 |

OTHER PUBLICATIONS

Carboni et al., AS601245 (1,3-Benzothiazol-2-yl (2-{[2-(3-pyridinyl) ethyl] amino}-4 pyrimidinyl) Acetonitrile): A c-Jun NH2-Terminal Protein Kinase Inhibitor with Neuroprotective Properties,avaiiable online on Feb. 26, 2004, available in print on Jul. 2004, Journal of Pharmacology and Experimental Therapeutics, vol. 310, No. 1, 25-32.*
Weinreb et al., Primary open-angle glaucoma, May 2004, The Lancet, vol. 363, Issue 9422, 1711-1720.*
Woodward et al., The inflow and outflow of anti-glaucoma drugs, May 2004, Trends in Pharmacological Sciences, vol. 25, issue 5, 238-241.*
Tripathi et al., Trabecular cell expression of fibronectin and MMP-3 is modulated by aqueous humor growth factors, Experimental Eye Research, vol. 78, Issue 3, Mar. 2004, pp. 653-660.*
Li et al., Fibronectin overexpression inhibits trabecular meshwork cell monolayer permeability, 2004, Molecular Vision, 10, 750-7.*
Adjei, "Blocking oncogenic Ras signaling for cancer therapy," J Natl Cancer Inst 93:1062-1074 (2001).
Amendola et al., "Postnatal changes in nerve growth factor and brain derived neurotrophic factor levels in the retina, visual cortex, and geniculate nucleus in rats with retinitis pigmentosa," Neurosci Lett 345:37-40 (2003).
Barres et al., "Immunological, morphological, and electrophysiological variation among retinal ganglion cells purified by panning," Neuron 1:791-803 (1988).
Bruckner et al., "JNK3 contributes to c-Jun activation and apoptosis but not oxidative stress in nerve growth factor-deprived sympathetic neurons," J Neurochem 78:298-303 (2001).
Clark & Pang, "Advances in Glaucoma Therapeutics," Expert Opin Emerging Drugs 7:141-163 (2002).
Gupta et al., "Selective interaction of JNK protein kinase isoforms with transcription factors," EMBO J 15:2760-2770 (1996).
Harris et al., "Progress in measurement of ocular blood flow and relevance to our understanding of glaucoma and age-related macular degeneration," Prog Retina Eye Res 18:669-687 (1999).
Hirosumi et al, "A central role for JNK in obesity and insulin resistance," Nature 420:333-337 (2002).
Hisatomi et al., "Critical role of photoreceptor apoptosis in functional damage after retinal detachment," Curr Eye Res 24:161-172 (2002).
Hollander and Vaaland, "A reliable staining method for semi-thin sections in experimental neuroanatomy," Brain Res 10:120-126 (1968).
Kwong and Caprioli, "Expression of phosphorylated c-Jun N-terminal protein kinase (JNK) in experimental glaucoma in rats," Experimental Eye Research, 82:576-582 (2006).

(Continued)

*Primary Examiner*—Frederick Krass
*Assistant Examiner*—Gigi Huang
(74) *Attorney, Agent, or Firm*—Jason J. Derry (57) ABSTRACT

Compositions and methods for lowering IOP and/or providing neuroprotection are disclosed. The compositions and methods are particularly directed to the use inhibitors of Jun N-terminal kinases (JNK) to lower IOP and/or provide neuroprotection.

3 Claims, 6 Drawing Sheets

OTHER PUBLICATIONS

Le-Niculescu et al., "Withdrawal of Survival Factors Results in activation of the JNK pathway in neuronal cells leading to Fas ligand induction and cell death," Mol Cell Biol 19:751-763 (1999).

Lewis et al., "Effects of neurotrophin brain-derived neurotrophic factor in an experimental model of retinal detachment," Invest Ophthalmol Vis Sci 40:1530-1544 (1999).

Manning & Mercurio, "Transcription inhibitors in inflammation," Exp Opin Invest Drugs 6:555-567 (1997).

Pang et al., "Age-dependent changes in ocular morphology of a spontaneous ocular hypertensive mouse strain (DBA/2J)," IOVS 40:S671 (1999).

Schumer et al., "The nerve of glaucoma!," Arch Ophthalmol 112:37-44 (1994).

Sherry & Townes-Anderson, "Rapid glutamtergic alterations in the neural retina induced by retinal detachment," Invest Ophthalmol Vis Sci 41:2779-2790 (2000).

Tao et al., "Encapsulated cell-based delivery of CNTF reduces photoreceptor degeneration in anima models of retinitis pigmentosa," Invest Ophthalmol Vis Sci 43:3292-3298 (2002).

Tournier et al., "Requirement of JNK for stress-induced activation of the cytochrome c-mediated death pathway," Science 288:870-874 (2000).

Van Buskirk et al., "Predicted outcome from hypotensive therapy for glaucomatous optic neuropathy," Am J Ophthalmol 25:636-640 (1993).

Xia et al., "Opposing effects of ERK and JNK-p38 MAP kinases on apoptosis," Science 270:1326-1331 (1995).

Yamada et al., "Fibroblast growth factor-2 decreases hyperoxia-induced photoreceptor cell death in mice," Am J Pathol 159:1113-1120 (2001).

Yang et al., "Absence of excitotoxicity-induced apoptosis in the hippocampus of mice lacking the JNK3 gene," Nature 389:865-870 (1997).

Fini M E et al., "Glaucomatous Trabecular Meshwork Cells Are Unresponsive To Treatment With Exogenous Interleukin-1". ARVO Annual Meeting Abstract Search And Program Planner, vol. 2003, Abstract #3167, Annual Meeting Of The Association For Research In Vision And Ophthalmology; Fort Lauderdale, Fl,; May 4-8, 2003.

PCT Internation Search Report for Internaitonal Application No. PCT/US2005/038825 mailed Sep. 19, 2006.

Kwong et al.; "Expression of phosphorylated c-June N-terminal protein kinase (JNK) in experimantal glaucoma in rats"; Experimental Eye Research, vol. 82, No. 4, pp. 576-582 (Apr. 2006).

Lutjen-Drecoll; "Morphological changes in glaucomatous eyes and the role of TGFB2 for the pathogenesis of the disease"; Experimental Eye Research; vol. 81; pp. 1-4 (2005).

Tamm and Fuchshofer; "What increases outflow resistance in primary open-angle glaucoma"; Survey of Ophthalmology; vol. 52; Supplement 2; pp. S101-S104 (2007).

Tripathi, et al.; "Aqueous humor in glaucomatous eyes contains an increased level of TGF-Beta2"; Experimental Eye Research; vol. 59; pp. 723-728 (1994).

Inatani et al.; "Transforming growth factor-beta2 levels in aqueous humor of glaucomatous eyes"; Graefe's Arch. Clin. Exp. Ophthalmology; vol. 239; pp. 109-113 (2001).

Ochiai and Ochiai; "Higher concentration of transforming growth factor-beta in aqueous humor of glaucomatous eyes and diabetic eyes"; Japan Journal of Ophthalmology; vol. 46; pp. 249-253 (2002).

Fleenor et al; "TGFbeta2-induced changes in human trabecular meshwork: implications for intraocular pressure"; Investigative Ophthalmology & Visual Science; vol. 47; No. 1; pp. 226-234 (Jan. 2006).

Zhao et al.; "Gene and protein expression changes in human trabecular meshwork cells treated with transforming growth factor-beta"; Investigative Ophthalmology & Visual Science; vol. 45; No. 11; pp. 4023-4034 (Nov. 2004).

Rahimi and Leof; "TGF-beta signaling: a tale of two responses"; Journal of Cellular Biochemistry; vol. 102; pp. 593-608 (2007).

Roux et al; K252a and CEP1347 are neuroprotective compounds that inhibit mixed-lineage kinase-3 and induce activation of Akt and ERK; The Journal of Biological Chemistry; vol. 277; No. 51; pp. 49473-49480 (12/20/002).

* cited by examiner

USE OF INHIBITORS OF JUN N-TERMINAL KINASES TO TREAT GLAUCOMA

This application is a continuation-in-part application of Ser. No. 11/259,566, filed Oct. 26, 2005, which claims priority to U.S. application Ser. No. 60/623,755, filed Oct. 29, 2004.

BACKGROUND OF THE INVENTION

1. Field of the Invention

The present invention relates generally to the field of glaucoma and, more specifically, to the use of inhibitors of Jun N-terminal kinases (JNK) to lower intraocular pressure and provide neuroprotection to patients suffering from glaucoma.

2. Description of the Related Art

Many pathological changes in the eye, such as glaucoma, acute ischemic optic neuropathy, macular degeneration, retinitis pigmentosa, retinal detachment, retinal tears or holes, and other ischemic retinopathies or optic neuropathies, cause injury or death of retinal neurons, which can lead to loss of vision. For example, primary open-angle glaucoma (POAG) is a progressive disease leading to optic nerve damage and ultimately blindness. The cause of this disease has been the subject of extensive studies for many years, but is still not fully understood. Glaucoma results in the neuronal degeneration of the retina and optic nerve. Even under optimal medical care and surgical treatment, it is still associated with a gradual loss of retinal ganglion cells (RGC), which causes a decline of visual function (Van Buskirk et al. (1993); Schumer et al. (1994)).

An abnormal increase in intraocular pressure (IOP) is a major risk factor of glaucoma. Currently, the only available treatment for glaucoma is to lower IOP either by medication or surgery. Lowering IOP is effective in slowing the development of POAG and delaying its damaging effects. Nonetheless, the loss of visual field in glaucoma patients does not always correlate with IOP, and lowering IOP alone does not completely stop the disease process.

There is not one mechanism that seems sufficient alone to explain the wide spectrum and patterns of pathological changes usually observed in glaucoma patients. It is probable that glaucoma involves more than one etiology and different mechanisms are manifested in different patients and/or different stages of the disease. Some of the more important proposals are: deprivation of neurotrophic factors, vascular abnormality (ischemia), and glutamate toxicity. These mechanisms eventually lead to apoptosis of the RGC (Clark & Pang (2002)).

The same mechanisms have been proposed to be involved in other ocular diseases. For example, a decrease in neurotrophic factors is associated with a rat model of retinitis pigmentosa (Amendóla et al. (2003)). Introduction of certain neurotrophic factors to the retina can reduce retinal damages related to retinitis pigmentosa (Tao et al. (2002)), retinal detachment (Hisatomi et al., (2002); Lewis et al. (1999)), and experimental macular degeneration (Yamada et al. (2001)). Retinal ischemia is involved in acute ischemic optic neuropathy, macular degeneration (Harris et al. (1999)), and other ischemic retinopathies or optic neuropathies. Similarly, glutamate toxicity may contribute to the retinal damages seen in retinal detachment (Sherry & Townes-Anderson (2000)).

U.S. Patent Application No. US2005/0069893 describes the measurement of JNK gene expression as a means of diagnosing glaucoma but does not discuss the use of inhibitors of JNK to lower intraocular pressure or to provide neuroprotection to a patient suffering from glaucoma.

Currently, no available therapy for glaucoma seeks to interrupt the mechanisms by which the ocular tissues are damaged in the disease process. Moreover, although a variety of therapeutic agents have been proposed as having the ability to lower ocular hypertension, many of these agents have associated side effects which may render them undesirable as ocular therapeutic agents. What is needed is a glaucoma treatment that addresses the underlying pathological cause of the disease and thereby provides a decrease in IOP and neuroprotection without resulting undesirable side effects typically associated with agents used to lower IOP.

SUMMARY OF THE INVENTION

The present invention overcomes these and other drawbacks of the prior art by providing compositions and methods for decreasing ocular hypertension and providing neuroprotection to patients suffering from glaucoma. The compositions and methods comprise at least one inhibitor of JNK to lower IOP and provide neuroprotection.

BRIEF DESCRIPTION OF THE DRAWINGS

The following drawings form part of the present specification and are included to further demonstrate certain aspects of the present invention. The invention may be better understood by reference to these drawings in combination with the detailed description of specific embodiments presented herein.

DETAILED DESCRIPTION OF PREFERRED EMBODIMENTS

The present invention is directed to compositions and methods for decreasing ocular hypertension, lowering intraocular pressure and/or providing neuroprotection to patients suffering from glaucoma. The compositions comprise one or more inhibitor(s) of JNK in a pharmaceutically acceptable vehicle.

Jun N-terminal kinases (JNK) are a family of stress-activated protein kinases comprising at least 10 isoforms created by alternative splicing of mRNA transcripts derived from three genes: JNK1, JNK2, and JNK3 (Gupta et al. (1996)). Activation of JNK is required for certain forms of stress-induced apoptosis (Tournier et al. (2000)), which leads to phosphorylation of a number of transcription factors and cellular proteins, particularly those associated with apoptosis (e.g., Bcl2, Bcl-$X_L$, p53, etc.). In cell culture, activation of JNK correlates with neuronal apoptosis induced by a variety of insults (Xia et al. (1995); Le-Niculescu et al. (1999)). JNK3 is required for sympathetic neuron death following trophic factor withdrawal (Bruckner et al. (2001)). Mice deficient in JNK3 are resistant to the hippocampal neurotoxicity induced by kainic acid (Yang et al. (1997)). Because of these neuroprotective actions, inhibitors of JNK have been proposed as treatment for degenerative diseases of the brain, such as, Alzheimer's disease, Parkinson's disease, stroke, and ischemia-induced brain dysfunction. In addition, because the JNK signaling pathway also regulates the activity and metabolism of some of the molecules involved in inflammation (Manning & Mercurio (1997)), JNK inhibitors were proposed as treatment for immune diseases, such as rheumatoid arthritis, asthma, chronic transplant rejection, inflammatory bowel disease, and multiple sclerosis. Other studies further indicate that JNK inhibitors may be useful as potential therapeutic agents for obesity, type 2 diabetes (Hirosumi et al. (2002)), and cancer (Adjei (2001)).

It is not obvious that JNK inhibitors, even with multiple pharmacological actions listed above, are useful in lowering intraocular pressure and providing neuroprotection. None of the above mentioned diseases have been shown to be associated with glaucoma, elevated intraocular pressure, or ocular neuroprotection. Moreover, the usefulness of a drug in the brain does not predict its usefulness in the eye, since therapeutic agents useful for degenerative diseases in the brain do not always protect against glaucomatous apoptotic death of RGC or other ocular diseases. Inflammation, immune abnormality, diabetes, obesity, or cancer is not widely accepted as an etiology of glaucoma, elevated intraocular pressure or ocular neuroprotection.

Figure 1:
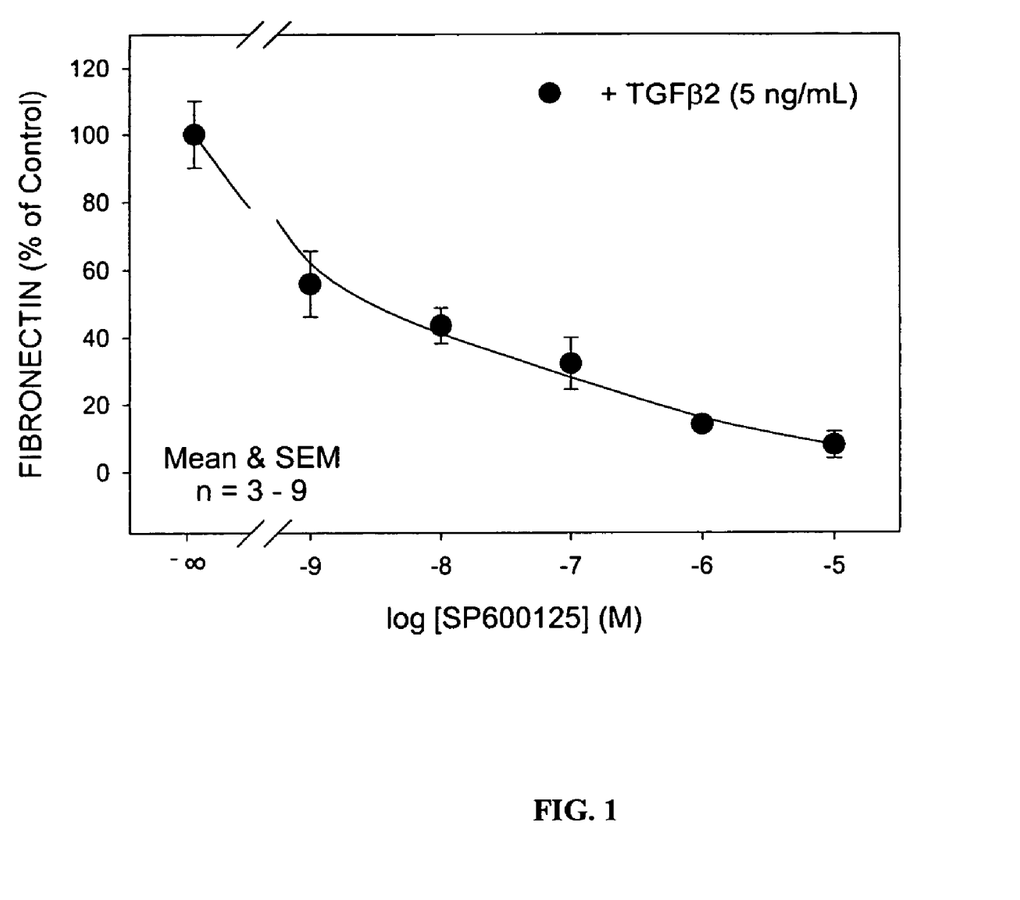
FIG. 1. Dose-dependent effects of SP600125 on TGFβ2-stimulated (24 h) increase of fibronectin level in supernatants from cultured human trabecular meshwork (GTM-3) cells.
Figure 2:
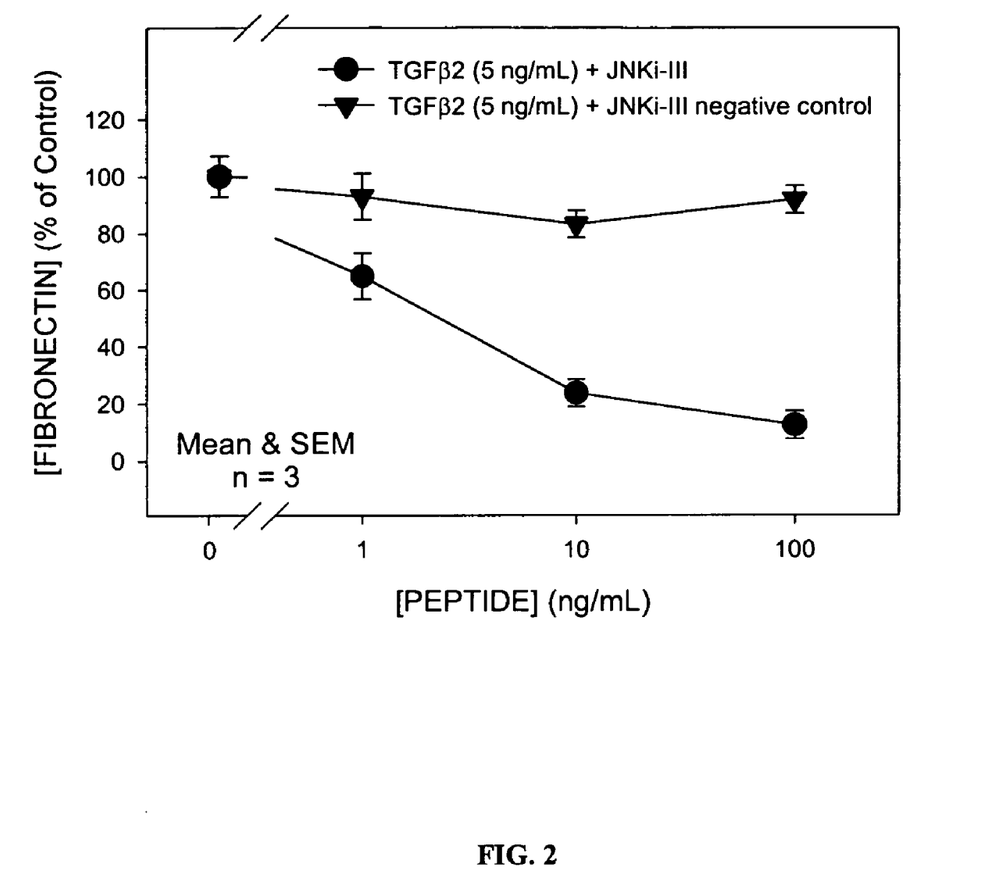
FIG. 2. Response to a selective, cell-permeable peptide inhibitor (JNKi-III; Calbiochem cat. # 420130) vs that of a cell-permeable negative (scrambled sequence) control peptide (Calbiochem, cat. # 420131). Both agents were tested for effect on TGFβ2-stimulated (24 h) increase of fibronectin level in supernatants from cultured human trabecular meshwork (GTM-3) cells.

Unexpectedly, the present inventors have discovered that inhibition of Jun N-terminal kinases (JNKi) significantly reduces transforming growth factor-beta2 (TGFβ2)-induced fibronectin expression by a human trabecular meshwork (TM) cell line (FIG. 1 and FIG. 2). Fibronectin is known to be a component of the TM's extracellular matrix (ECM) and an over accumulation of ECM in the TM region is a hallmark of many forms of glaucoma. Such increases are believed to lead to increased resistance to aqueous outflow, thereby elevating intraocular pressure (IOP). JNK has also been implicated in the signaling pathway for TGFβ-mediated production of connective tissue growth factor (CTGF) (Utsugi et al. 2003). CTGF may play a role in IOP elevation in that it is known to increase accumulation of various ECM components, including fibronectin.

It has been shown that a non-peptide JNK inhibitor, SP-600125, was protective against glutamate-induced or trophic factor withdrawal-induced death of a rat retinal neuron, the RGC, in culture (see co-pending U.S. application Ser. No. 11/259.566). The compound was also found to be protective against ischemia/reperfusion-induced optic neuropathy in the rat. Since deprivation of trophic factors, ischemia, and glutamate toxicity were proposed as potential mechanisms of glaucoma and various ocular diseases, these data indicate that non-peptide JNK inhibitors are useful as therapeutic agents for providing neuroprotection for ocular tissues.

As used herein, "inhibitors of JNK" refers to those compounds which can decrease the activity of JNK to 50% or lower of the control value. The potential inhibitory effect of compounds on JNK activity can be easily evaluated by those skilled in the art. Many JNK activity assay kits are commercially available, e.g., Stratagene catalog # 205140, Upstate catalog # 17-166, etc. In preferred aspects, the JNK inhibitors for use in the compositions and methods of the present invention may be small molecules, peptides, peptidomimetics, antibodies, etc. Most preferably, the JNK inhibitors will be small molecules.

Examples of JNK inhibitors expected to be useful in the methods and compositions of the present invention include, but not are limited to, SP600125 and pharmacologically active compounds disclosed in patent applications numbers WO200035906, WO200035909, WO200035921, WO200064872, WO200112609, WO200112621, WO200123378, WO200123379, WO200123382, WO200147920, WO200191749, WO2002046170, WO2002062792, WO2002081475, WO2002083648, WO2003024967; all of which are hereby incorporated by reference.

Additional preferred JNK inhibitors expected to be useful in the methods and compositions of the invention include AS601245 (Ferrandi et al., 2004).

CEP-1347 (KT7515) (Maroney et al. 1998; Roux et al. 2002).

K252a (Roux et al., 2002).

The methods comprise administering one or more JNK inhibitors to a human patient to decrease ocular hypertension, or lower intraocular pressure and provide neuroprotection.

The JNK inhibitors of the present invention may be contained in various types of pharmaceutical compositions, in accordance with formulation techniques known to those skilled in the art. In general, the JNK inhibitors will be formulated in solutions or suspensions for topical ophthalmic or intraocular administration, or as tablets, capsules or solutions for systemic administration (e.g., oral or intravenous).

Oral formulations of the JNK inhibitors are preferred due to ease of administration. Oral formulations may be in liquid or solid form. In general, oral formulations will include the active JNK inhibitor and inert excipients. In general, solid tablet or capsule dosages will contain various excipients such as bulking agents, binding agents, time release coatings, and so on. Liquid dosages will contain carriers, buffers, tonicity agents, solubilizing agents, and so on.

In general, the doses utilized for the above described purposes will vary, but will be in an effective amount to inhibit or ameliorate retinal neuropathy. As used herein, the term "pharmaceutically effective amount" refers to that amount which lowers intraocular pressure and inhibits or ameliorates retinal neuropathy. The JNK inhibitors will normally be contained in these formulations in an amount from about 0.01 to about 10.0 weight/percent. Preferable concentrations range from about 0.1 to about 5.0 weight/percent. For topical administration, these formulations are delivered to the disease site one to six times a day, depending on the routine discretion of the skilled clinician. Systemic administration, for example, in the form of tablets or liquid useful for the treatment will contain about 10-1000 mg of a JNK inhibitor, and can be taken 1-4 times per day depending on the discretion of the skilled clinician.

As used herein, the term "pharmaceutically acceptable carrier" refers to any formulation which is safe, and provides the appropriate delivery for the desired route of administration of an effective amount of at least one JNK inhibitor of the present invention.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Fibronectin Assay

Cultured transformed human TM cells were used in these studies. Generation and characterization of the GTM-3 transformed cell line has been previously described. [Pang I H, et al., Curr Eye Res. 1994; 13:51-63]. Maintenance growth medium consisted of Dulbecco's modified Eagle's medium with Glutamax I (Gibco/BRL, Grand Island, N.Y.) supplemented with 10% fetal bovine serum (Hyclone, Logan, Utah) and 50 µg/mL gentamicin (Gibco/BRL). For assay, cultures were trypsinized and seeded into 24-well plates (Corning Costar, Acton, Mass.) and allowed to grow until monolayers reached approximately 90% confluence. Culture medium was then replaced with 0.25 mL serum- and antibiotic-free medium containing the appropriate test compound(s). Cells were incubated 24 h, at 5% $CO_2$ and 37° C. Aliquots of culture supernatants were then assayed for fibronectin content by ELISA.

In experiments assessing the effects of the JNK inhibitor, SP600125, the cells were cultured concurrently with the compound and with TGFβ2 (5 ng/mL). TGFβ2 is a known inducer of fibronectin production by TM cells. SP600125 caused a dose-dependent reduction in the level of fibronectin in TGFβ2-treated GTM-3 cell supernatants. These results are illustrated in FIG. 1. The role of JNK was further elucidated by use of a selective, cell-permeable peptide inhibitor of JNK. As with SP600125, co-incubation with the peptide inhibitor caused a dose-dependent reduction in the level of fibronectin in TGFβ2-treated GTM-3 cell supernatants. These results contrast with a lack of effect of a cell-permeable negative (scrambled sequence) control peptide, thus corroborating the central role of JNK in these studies. Results with these peptides are illustrated in FIG. 2.

EXAMPLE 2

The following example demonstrates the protective efficacy of a JNK inhibitor against cytotoxic insults to retinal cells.

Rat Retinal Ganglion Cell Survival Assay

Adult Sprague-Dawley rats were euthanized by $CO_2$ asphyxiation. Their eyes were enucleated and placed in Dulbecco's modified Eagle's medium: Nutrient mixture F12 (1:1; DMEM/F12). The retinas were incubated in a papain solution, containing papain (34 units/mL), DL-cysteine (3.3 mM), and bovine serum albumin (0.4 mg/ml) in DMEM/F12, for 25 min at 37° C. Retinal pieces were then triturated until cells were dispersed. Cell suspension (1.5 ml; containing approximately $4.5 \times 10^6$ cells) was placed into each of the poly-D-lysine coated glass bottom culture dishes. The cells were cultured in a culture medium previously described by Barres et al. (1988) for 3 days in 95% air/5% $CO_2$ at 37° C.

In experiments assessing the toxicity of glutamate on cell survival, the cells were cultured with 100 µM glutamate for 3 days. In experiments assessing the detrimental effect of neurotrophic factor withdrawal on cell survival, basic fibroblast growth factor, brain-derived trophic factor, and ciliary-derived neurotrophic factor were removed from the medium and cells cultured for 3 days. In experiments assessing the potential protective effects of a JNK inhibitor, SP600125, the cells were cultured with the compound in the presence of the glutamate or in the absence of the indicated trophic factors for 3 days. At the end of the 3-day culture period, the cells were immunostained for Thy-1, a cell surface marker for RGC, and observed under a fluorescent microscope. Thy-1-positive cells were counted and averaged. The results are illustrated in FIG. 3.

Figure 3:
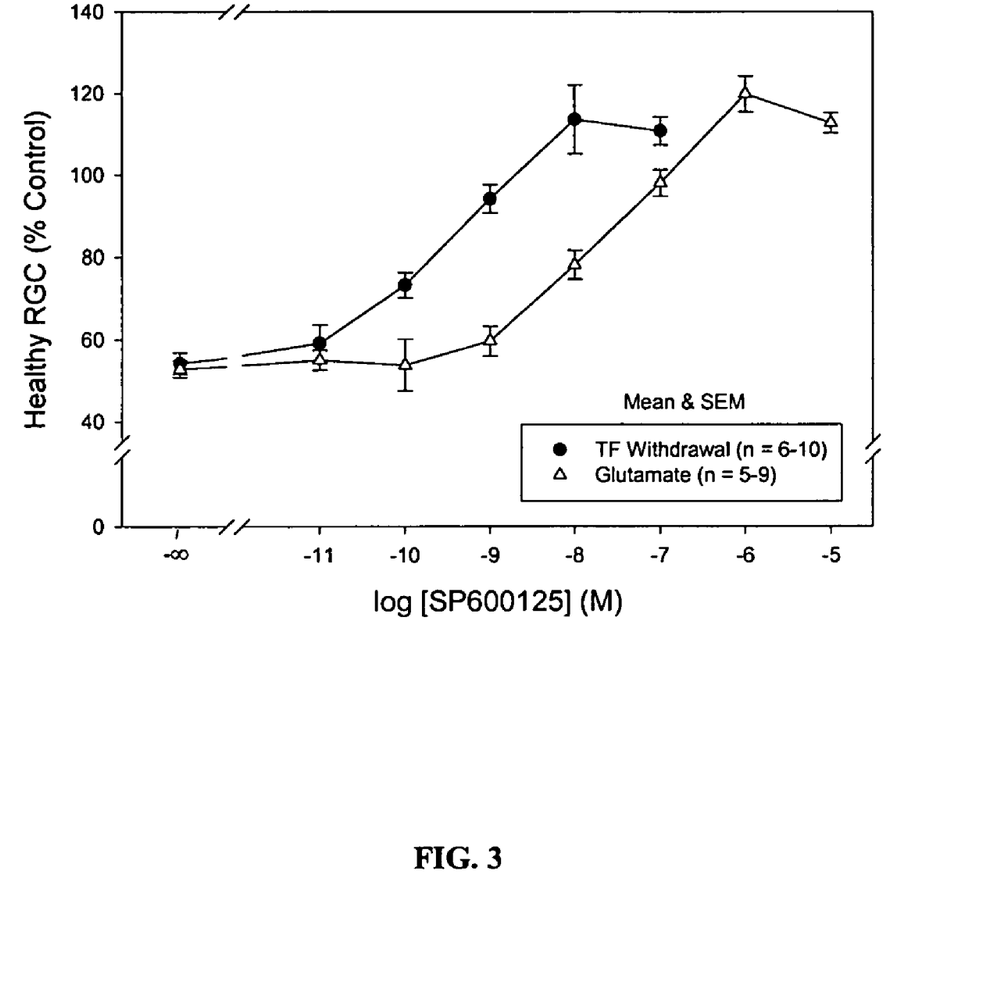
FIG. 3. Effect of SP600125 on rat RGC survival with or without trophic factors, with or without glutamate (100 μM). The cells were cultured with the respective conditions for 3 days. Survival was quantified by counting all Thy-1 positive healthy cells.

FIG. 3 illustrates that the survival of RGC depended on the presence of the indicated neurotrophic factors, such that removal of the neurotrophic factors (TF Withdrawal) from the culture medium caused death of RGC to approximately 50% of the control group. Incubation of the cells with SP600125 significantly and completely protected the cells against such insult. FIG. 3 also shows that glutamate was toxic to the RGC, since addition of 100 µM glutamate to the culture medium decreased cell survival by approximately 50%. Again, incubation of the cells with SP600125 also significantly and completely protected the cells against this cytotoxicity.

EXAMPLE 3

The following example demonstrates the protective efficacy of a JNK inhibitor against ischemia-induced optic neuropathy in the rat.

Ischemia/Reperfusion-Induced Optic Neuropathy in the Rat

Adult Wistar rats were anesthetized and the anterior chamber of one eye of each animal was cannulated. The cannula was connected to a raised saline reservoir whose height was adjusted to produce an ocular pressure that was higher than the systolic pressure of the animal, which, by stopping retinal blood flow, produced retinal ischemia. After 60 minutes of ischemia, the intracameral cannula was removed to allow reperfusion of the retina. Two weeks later, the rats were euthanized, their optic nerves isolated, fixed in 2% paraformaldehyde, 2.5% glutaraldehyde in 0.1 M cacodylate buffered solution, sectioned, and stained in 1% p-phenylenediamine in isopropanol:methanol (1:1) prepared as described by Hollander and Vaaland (1968). The optic nerve damage in each optic nerve section was ranked by an Optic Nerve Damage Score as previously reported by Pang et al. (1999). In this ranking system, a score of 1 represented no damage, and a score of 5 represented total damage.

To test the potential protective effect of SP600125, selected animals were treated with a daily intraperitoneal injection of SP600125 (30 mg/kg) for 16 consecutive days starting 2 days before ischemia was induced. The results are illustrated in FIG. 4.

Figure 4:
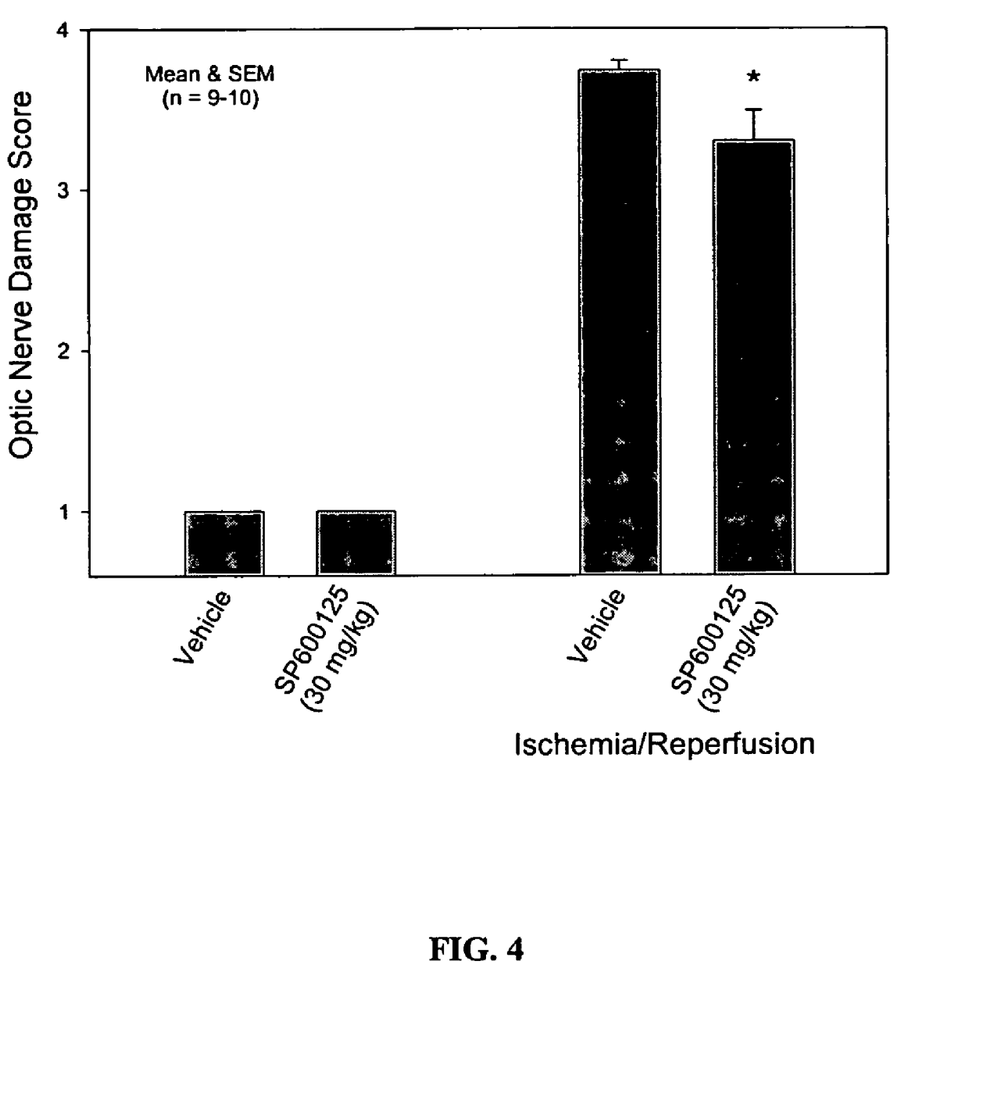
FIG. 4. Effect of SP600125 on ischemia/reperfusion-induced optic neuropathy. An optic nerve damage score of 1 represented no damage, and a score of 5 represented total damage. *: $p<0.05$ versus the vehicle-treated group by Student's t-test.

FIG. 4 shows that ischemia/reperfusion caused significant damage to the optic nerve as indicated by a dramatic increase in the optic nerve damage score. It also demonstrates that systemic administration of SP600125 could protect against this ischemic insult to the retina as shown by a significant reduction in the optic nerve damage score.

EXAMPLE 4

A JNK inhibitor, SP600125, was tested in cultured adult rat retinal ganglion cells (RGC). It was shown to protect against both glutamate-induced and trophic factor withdrawal-induced cytotoxicity.

Methods

A. RGC Culture

Adult Sprague-Dawley rats were euthanized by $CO_2$ asphyxiation. Their eyes were enucleated and the retinas isolated. Retinal cells were treated with of papain solution for 25 min at 37° C., then washed 3 times with 5 mL RGC culture medium (Neurobasal medium with various nutrient supplements+1% fetal calf serum). Retinal cells were dispersed by trituration. Cell suspension was placed onto poly-D-lysine- and laminin-coated 8-well chambered culture slides. The cells were then cultured in 95% air/5% $CO_2$ at 37° C.

B. Cytotoxic Insults

For glutamate-induced toxicity studies, cells were pretreated with vehicle or the indicated compounds for 30 minutes, followed by 100 μM glutamate for 3 days.

For trophic factor withdrawal studies, three trophic factors, basic fibroblast growth factor, brain-derived neurotrophic factor, and ciliary neurotrophic factor, were removed from the culture medium. Cells were cultured in this medium with the indicated compounds for 3 days.

C. Quantification of Cell Survival

At the end of the incubation period, the cells were fixed and labeled for Thy-1, a RGC marker, by immunocytochemistry. Cell survival was quantified by manually counting Thy-1-positive healthy cells in each well.

Results

A. Effect of SP600125 on Glutamate-Induced Toxicity in Rat RGC

Figure 5:
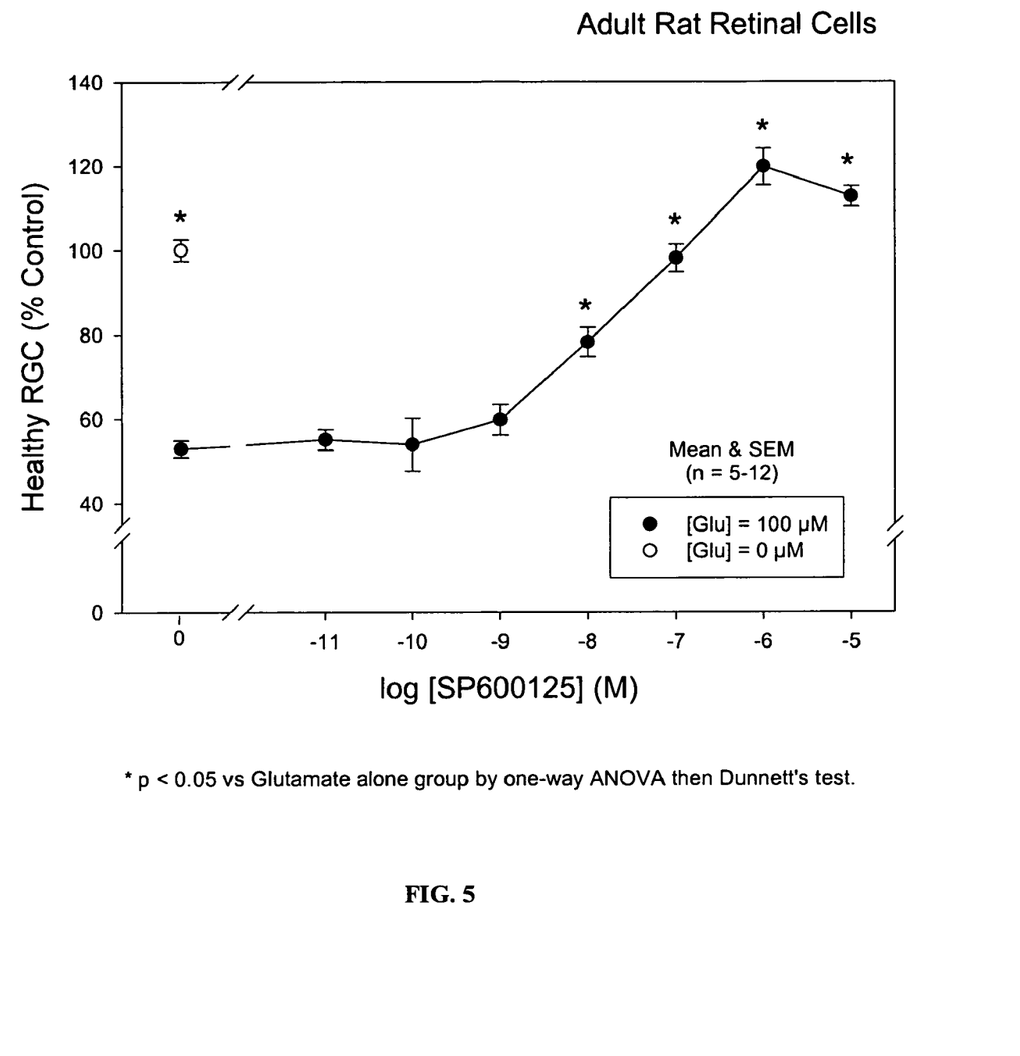
FIG. 5. Effects of SP600125 on the survival of cultured adult rat RGC. The cells were treated with glutamate (100 μM) with or without SP600125 for 3 days.

It has been previously shown that glutamate was toxic to rat RGC; only 50-70% of cells survived after a 3-day treatment of 100 μM glutamate. The glutamate-induced toxicity in these cells can be prevented by pretreatment with MK801. SP600125 was protective against this insult in a dose-dependent manner (FIG. 5).

B. Effect of SP600125 on Trophic Factor Withdrawal-Induced Toxicity in RGC

Figure 6:
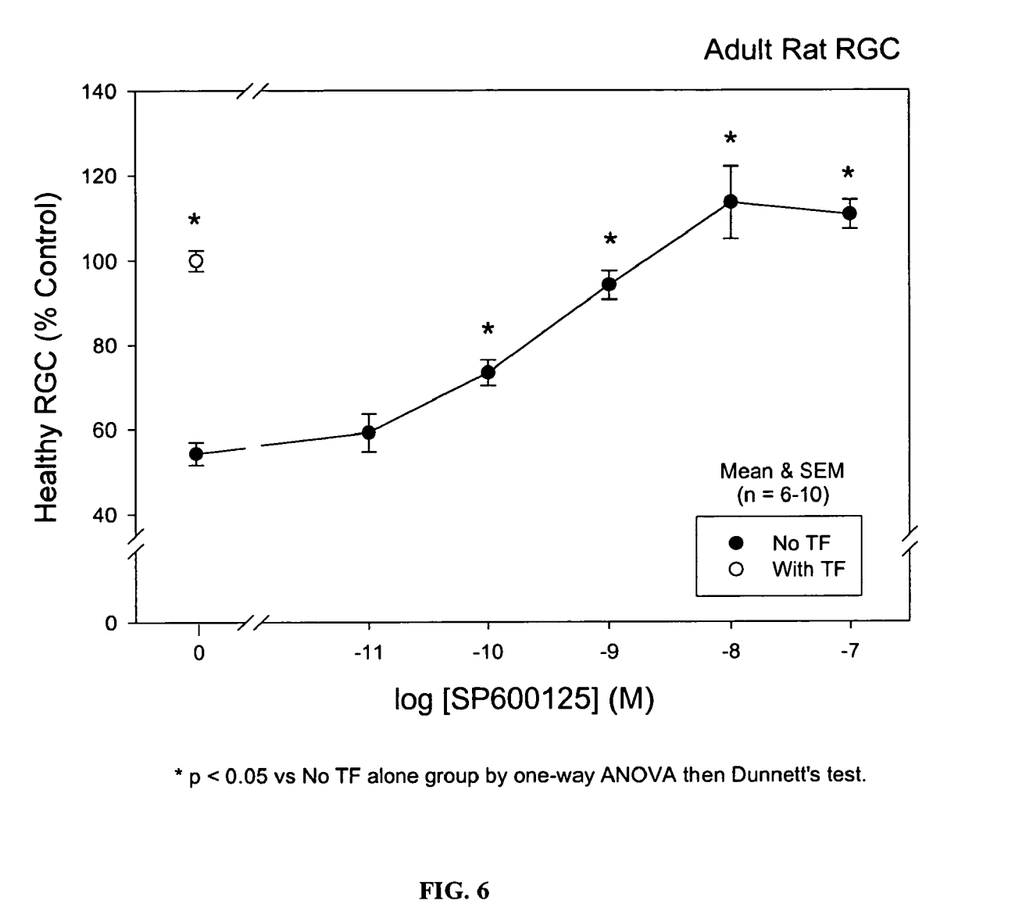
FIG. 6. Effects of SP600125 on the survival of cultured adult rat RGC. Selected trophic factors (bFGF, BDNF, CNTF) were withdrawn from all wells except the controls. The cells were treated with the indicated concentrations of SP600125 for 3 days. (TF=trophic factors).

Previously, it was shown that removal of the three trophic factors for 3 days caused death of approximately 40-50% of the cells. SP600125 was protective against this insult in a dose-dependent manner (FIG. 6).

EXAMPLE 5

Topical compositions useful for treating glaucoma and other ocular diseases:

| Component | Wt. % |
|---|---|
| JNK inhibitor | 0.1-5 |
| HPMC | 0.01-10 |
| Benzalkonium Chloride | 0.005-0.5 |
| Sodium Chloride | 0.5-2.0 |
| Edetate Disodium | 0.005-0.5 |
| NaOH/HCl | q.s. pH 7.4 |
| Purified Water | q.s. 100 mL |

The above formulation is prepared by first placing a portion of the purified water into a beaker and heating to 90° C. The hydroxypropylmethylcellulose (HPMC) is then added to the heated water and mixed by means of vigorous vortex stirring until all of the HPMC is dispersed. The resulting mixture is then allowed to cool while undergoing mixing in order to hydrate the HPMC. The resulting solution is then sterilized by means of autoclaving in a vessel having a liquid inlet and a hydrophobic, sterile air vent filter.

The sodium chloride and the edetate disodium are then added to a second portion of the purified water and dissolved. The benzalkonium chloride is then added to the solution, and the pH of the solution is adjusted to 7.4 with 0.1M NaOH/ HCl. The solution is then sterilized by means of filtration.

SP600125 is sterilized by either dry heat or ethylene oxide. If ethylene oxide sterilization is selected, aeration for at least 72 hours at 50° C. is necessary. The sterilized compound is weighed aseptically and placed into a pressurized ballmill container. Sterilized glass balls are then added to the container and the contents of the container are milled aseptically at 225 rpm for 16 hours, or until all particles are in the range of approximately 5 microns.

Under aseptic conditions, the micronized drug suspension or solution formed by means of the preceding step is then poured into the HPMC solution with mixing. The ballmill container and balls contained therein are then rinsed with a portion of the solution containing the sodium chloride, the edetate disodium and benzalkonium chloride. The rinse is then added aseptically to the HPMC solution. The final volume of the solution is then adjusted with purified water and, if necessary, the pH of the solution is adjusted to pH 7.4 with NaOH/HCl.

EXAMPLE 6

Preferred Formulation for Topical Administration:

| Component | Wt. % |
|---|---|
| JNK inhibitor | 0.1-5 |
| HPMC | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. 100 mL |

EXAMPLE 7

Formulation for Oral Administration:
Tablet:
1-1000 mg of a JNK inhibitor with inactive ingredients such as starch, lactose and magnesium stearate can be formulated according to procedures known to those skilled in the art of tablet formulation.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. All such substitutions and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Patents and Published Patent Applications

WO200035906
WO200035909
WO200035921
WO200064872
WO200112609
WO200112621
WO200123378
WO200123379
WO200123382
WO200147920
WO200191749
WO2002046170
WO2002062792
WO2002081475
WO2002083648
WO2003024967

Other Publications

Adjei, "Blocking oncogenic Ras signaling for cancer therapy," J NATL CANCER INST 93:1062-1074 (2001).

Amendola et al., "Postnatal changes in nerve growth factor and brain derived neurotrophic factor levels in the retina, visual cortex, and geniculate nucleus in rats with retinitis pigmentosa," NEUROSCI LETT 345:37-40 (2003).

Barres et al., "Immunological, morphological, and electrophysiological variation among retinal ganglion cells purified by panning," NEURON 1:791-803 (1988).

Bruckner et al., "JNK3 contributes to c-Jun activation and apoptosis but not oxidative stress in nerve growth factor-deprived sympathetic neurons," J NEUROCHEM 78:298-303 (2001).

Clark & Pang, "Advances in Glaucoma Therapeutics," EXPERT OPIN EMERGING DRUGS 7:141-164 (2002).

Ferrandi et al., "Inhibition of c-Jun N-terminal kinase decreases cardiomyocyte apoptosis and infarct size after myocardial ischemia and reperfusion in anaesthetized rats," BRIT. J. PHARM. 142:953-960 (2004).

Gupta et al., "Selective interaction of JNK protein kinase isoforms with transcription factors," EMBO J. 15:2760-2770 (1996).

Harris et al., "Progress in measurement of ocular blood flow and relevance to our understanding of glaucoma and age-related macular degeneration," PROG RETINA EYE RES 18:669-687 (1999).

Hirosumi et al, "A central role for JNK in obesity and insulin resistance," NATURE 420:333-337 (2002).

Hisatomi et al., "Critical role of photoreceptor apoptosis in functional damage after retinal detachment," CURR EYE RES 24:161-172 (2002).

Hollander and Vaaland, "A reliable staining method for semi-thin sections in experimental neuroanatomy," BRAIN RES 10:120-126 (1968).

Le-Niculescu et al., "Withdrawal of survival factors results in activation of the JNK pathway in neuronal cells leading to Fas ligand induction and cell death," MOL CELL BIOL 19:751-763 (1999).

Lewis et al., "Effects of neurotrophin brain-derived neurotrophic factor in an experimental model of retinal detachment," INVEST OPHTHALMOL VIS SCI 40:1530-1544 (1999).

Manning & Mercurio, "Transcription inhibitors in inflammation," EXP OPIN INVEST DRUGS 6:555-567 (1997).

Maroney et al., "Motoneuron Apoptosis is Blocked by CEP-1347 (KT 7515), a Novel Inhibitor of the JNK Signaling Pathway," J. NEUROSCIENCE 18(1):104-111 (1998).

Pang et al., "Preliminary characterization of a transformed self strain derived from human trabecular meshwork," CURR. EYE RES. 13:51-63 (1994).

Pang et al., "Age-dependent changes in ocular morphology of a spontaneous ocular hypertensive mouse strain (DBA/2J)," INVEST OPHTHALMOL VIS RES 40:S671 (1999).

Roux et al., "K252a and CEP1347 are neuroprotective compounds that inhibit mixed-lineage kinase-3 and induce activation of Akt and ERK," J. BIOL. CHEM. 277(51):49473-49480 (2002).

Schumer et al., "The nerve of glaucoma!," ARCH OPHTHALMOL 112:37-44 (1994).

Sherry & Townes-Anderson, "*Rapid glutamtergic alterations in the neural retina induced by retinal detachment*," INVEST OPHTHALMOL VIS SCI 41:2779-2790 (2000).

Tao et al., "*Encapsulated cell-based delivery of CNTF reduces photoreceptor degeneration in anima models of retinitis pigmentosa*," INVEST OPHTHALMOL VIS SCI 43:3292-3298 (2002).

Tournier et al., "*Requirement of JNK for stress-induced activation of the cytochrome c-mediated death pathway*," SCIENCE 288:870-874 (2000).

Utsugi et al., *Am. J. Respir. Cell Mol. Biol.*, 28:754-761 (2003).

Van Buskirk et al., "*Predicted outcome from hypotensive therapy for glaucomatous optic neuropathy*," AM J OPHTHALMOL 25:636-640 (1993).

Xia et al., "*Opposing effects of ERK and JNK-p38 MAP kinases on apoptosis*," SCIENCE 270:1326-1331 (1995).

Yamada et al., "*Fibroblast growth factor-2 decreases hyperoxia-induced photoreceptor cell death in mice*," AM J PATHOL 159:1113-1120 (2001).

Yang et al., "*Absence of excitotoxicity-induced apoptosis in the hippocampus of mice lacking the JNK3 gene*," NATURE 389:865-870 (1997).

We claim:

1. A method for decreasing ocular hypertension, which comprises administering to a human patient identified as having glaucoma a composition comprising an effective amount of a JNK inhibitor and a pharmaceutically acceptable vehicle, wherein the JNK inhibitor is 2. A method according to claim 1, wherein the composition is an oral formulation.

3. A method according to claim 1, wherein the composition is a topical ophthalmic, surgical irrigating solution or an intraocular formulation.

* * * * *